United States Patent
U et al.

(10) Patent No.: US 6,635,064 B2
(45) Date of Patent: Oct. 21, 2003

(54) NON-SCATTERABLE, RADIO-OPAQUE MATERIAL FOR MEDICAL IMAGING APPLICATIONS

(75) Inventors: Hoi Sang U, San Diego, CA (US); James Peter Amis, Carlsbad, CA (US)

(73) Assignee: MacroPore Biosurgery, Inc., San Diego, CA (US)

( * ) Notice: Subject to any disclaimer, the term of this patent is extended or adjusted under 35 U.S.C. 154(b) by 0 days.

(21) Appl. No.: 09/971,279

(22) Filed: Oct. 4, 2001

(65) Prior Publication Data

US 2002/0095162 A1 Jul. 18, 2002

Related U.S. Application Data

(60) Provisional application No. 60/237,784, filed on Oct. 4, 2000.

(51) Int. Cl.[7] .................................................. A61B 19/00
(52) U.S. Cl. ........................ 606/130; 600/431; 600/424
(58) Field of Search ................................. 606/130, 129, 606/116, 1, 151, 142, 143; 600/414, 417, 424, 426, 429, 431

(56) References Cited

U.S. PATENT DOCUMENTS

| | | | |
|---|---|---|---|
| 4,826,487 A | * | 5/1989 | Winter ........................ 604/175 |
| 5,507,766 A | | 4/1996 | Kugo et al. |
| 5,916,193 A | | 6/1999 | Stevens et al. |
| 6,161,034 A | * | 12/2000 | Burbank et al. ............ 600/431 |
| 6,214,019 B1 | * | 4/2001 | Manwaring et al. ........ 606/130 |
| 6,261,260 B1 | | 7/2001 | Maki et al. |
| 6,356,782 B1 | * | 3/2002 | Sirimanne et al. .......... 600/431 |
| 6,524,345 B1 | | 2/2003 | Valimaa et al. |

OTHER PUBLICATIONS

Vaajanen et al., Expansion and Fixation Properties of a New Braided . . . , Mar. 2003., The Journal of Urology.

* cited by examiner

*Primary Examiner*—Pedro Philogene
(74) *Attorney, Agent, or Firm*—Stout, Uxa, Buyan & Mullins, LLP

(57) ABSTRACT

A marker assembly formed of a carbon fiber composition is disclosed. The marker assembly includes a shaft sized and shaped to be inserted into an organ, wherein the shaft includes a proximal end, a distal end, and a longitudinal axis extending between the proximal end and the distal end. The distal end of the shaft is sized and shaped to be positioned near a target region within the organ, and the shaft includes a lumen extending through the shaft in a direction parallel to the longitudinal axis of the shaft. The lumen is constructed to accommodate a needle therethrough, so that the needle enters through the proximal end of the shaft, extends through the shaft, and exits through the distal end of the shaft. The marker assembly can also include other radiopaque or semi-radiopaque materials that provide higher definition imaging than titanium, when implanted within the organ.

16 Claims, 1 Drawing Sheet

NON-SCATTERABLE, RADIO-OPAQUE MATERIAL FOR MEDICAL IMAGING APPLICATIONS

BACKGROUND OF THE INVENTION

1. Field of the Invention

The present invention relates generally to medical devices and, more particularly, to materials and devices for use in medical imaging applications.

2. Description of Related Art

Stereotactic surgery involves the use of a precision apparatus and guided placement of surgical instruments to enable the surgeon to target precisely a structure within a bodily organ, such as the brain. Stereotaxic surgery may involve accurate localization of targets within the brain, for example, to insert electrodes for treatment of various neurological diseases (thalamotomy, pallidotomy, or insertion of brain stimulators to treat Parkinson's disease or tremor) or pain (particularly cancer pain), or to guide the surgeon to resect brain tumors with accuracy in order to optimize tumor removal and to minimize injury to surrounding brain tissue. Stereotactic radiosurgery or stereotactic radiotherapy uses similar localizing techniques to guide radiation to specifically confined areas within the brain.

A common stereotactic surgical technique includes a step of first identifying the target organ by imaging means such as a computerized axial tomography (CAT) scan using X-rays or a magnetic resonance imaging (MRI) scan. A stabilized insertion platform is affixed exteriorly to the body to hold a cannula or other locator device in fixed relation to the target organ. In the case of brain surgery a halo device is typically used as a stabilized insertion platform. The halo device may comprise any structure that is rigidly affixed to the cranium to hold a cannula or other device in fixed relation to the skull. A probe that is connected to the stabilized insertion platform is directed into an intra-cranial region of the cranium, based on predetermined coordinates derived from earlier diagnostic analysis for example. The predetermined coordinates may represent an approximation of a target location within the brain. Prior art analytical and medical instrumentation and procedures, which are suitable for stereotaxic surgery, are well known and for the sake of simplicity will not be detailed further herein.

Despite their widespread use, a certain margin of error in localization exists with prior-art stereotactic surgical procedures. This error may vary, for example, from 1 mm to 5 mm. Therefore, when precise localization is required, refinement of existing technology may be desired.

SUMMARY OF THE INVENTION

The present invention provides an apparatus and method for more accurately positioning instrumentation in an organ, such as a brain, of a patient. The apparatus is straightforward in design and construction and can be used with existing technology without requiring a substantial level of increased surgical skill.

In accordance with an aspect of the present invention, a marker assembly is formed of a carbon fiber composition to provide enhanced, high-definition imaging. The marker assembly includes a shaft sized and shaped to be inserted into an organ, wherein the shaft includes a proximal end, a distal end, and a longitudinal axis extending between the proximal end and the distal end. The distal end of the shaft is sized and shaped to be positioned near a target region within the organ, and the shaft includes a lumen extending through the shaft in a direction parallel to the longitudinal axis of the shaft. The lumen is constructed to accommodate a needle therethrough, so that the needle enters through the proximal end of the shaft, extends through the shaft, and exits through the distal end of the shaft. The marker assembly can also include other radiopaque or semi-radiopaque materials that provide higher definition imaging than titanium when implanted within the organ.

BRIEF DESCRIPTION OF THE DRAWINGS

The objects and advantages of the present invention will be more readily appreciated and understood with respect to the following detailed description, when considered in conjunction with the accompanying drawings of which.

DETAILED DESCRIPTION OF THE PRESENTLY PREFERRED EMBODIMENTS

Figure 1:
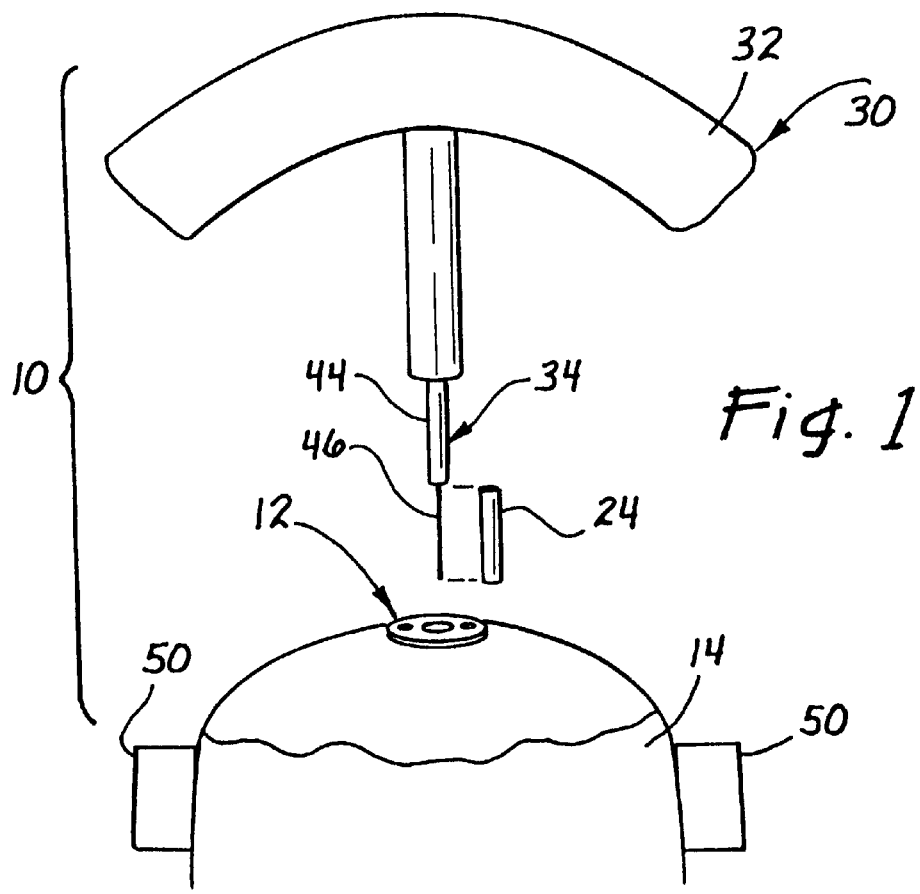
FIG. 1 illustrates a diagram of a system in accordance with the present invention, the system generally including an attachment member and a carbon-fiber marker assembly adapted to be removably connected to a stereotaxic locator device.

The present invention discloses new materials for use in stereotaxic procedures, as well as for use in any other type of imaging procedure, such as an MRI procedure, a CAT scan procedure or an X-ray procedure. In accordance with the present invention, probes and pointers suitable for use in imaging procedures are constructed of carbon fiber compositions as set forth herein. The surgeon can aim for any point within a mass or lesion, or can direct the surgery by using a series of stereotaxic points to outline the abnormal area. A carbon-fiber composition guide cannula can then be inserted into the target organ and used to guide probes, electrodes, drug delivery, etc. to the target site within the organ. The accuracy of placement of the guide cannula may subsequently be verified through a second radio-imaging scan, such as a CAT scan or MRI scan, in accordance with one aspect of the present invention. The materials of the present invention may also be used, for example, in endoscopic and other procedures.

MRI imaging techniques, for example, rely on the response of magnetic fields to produce computer images that provide positional, structural and/or biochemical information about tissue. Because of the strong magnetic fields used in MRI, prior-art stereotactic needles and pointers generally have not been available for use during the actual MRI scanning procedure. To the extent used in such imaging procedures, if any, and to the extent these materials would comprise non-ferromagnetic materials (e.g., titanium), the materials would still be susceptible to causing scattering or otherwise distorting or interfering with the image by, for example, causing a 2 mm diameter cannula to appear to be a 3.5 or 4 mm diameter cannula.

The marker or cannula of the present invention is constructed to be operable commensurately in time with imaging procedures and to minimize or eliminate detectable scattering or distortion. In accordance with the present invention, the markers, cannulas or pointers are constructed to comprise radiopaque or semi-radiopaque materials, that are selected or tailored in accordance with the selected imaging technique to provide higher definition imaging than titanium.

In accordance with the present invention, there is provided a cannula which comprises a bio-compatible carbon-fiber composite material which during imaging can result in a clear or clearer image, relative to the image that would be produced by a titanium object or cannula. It has been discovered that use of such a composite material, in the form of a 2 mm diameter needle, for example, can cause little or no scattering while producing a satisfactory image.

Composite carbon-fiber materials that can be used in accordance with the present invention preferably comprise carbon fibers and a binding resin to form a matrix. The carbon and fiber components can comprise 40–60% of the matrix and the balance can be comprised of resin. In modified embodiments, other materials, such as plastic, titanium, aluminum, brass or other alloy metals, or other materials that are not ferromagnetic, or other suitable materials known now or in the future, may be used in combination with the carbon-fibers and/or resin. The composites are preferably fabricated by orienting or directionally aligning the carbon fiber component or components, which may be necessary, for example, in order to achieve adequate fiber strength and enhance the mechanical properties of the composite.

Fabricating the composite with the desired fiber orientation may in accordance with one aspect of the present invention be more readily accomplished by the use of continuous carbon fiber. Such fiber may be preferred over discontinuous fibers for these applications, in accordance with one aspect of the present invention. The primary forms of continuous fiber employed in the composite fabrication include woven textile fabric or unidirectional tapes for use in lay-up structures, and continuous fiber yarn or tow, which are used for filament winding and in braided structures.

It is intended that the term "carbon-fiber" should include both graphite and non-graphite carbon fibers as well as monolithic graphite and non-graphite carbon. The carbon reinforcements preferably comprise a multi-dimensional network of carbon fiber material in a carbonized form, e.g., as carbon or graphite yarn, arranged in a plurality of groups, each comprising a plurality of yarns arranged parallel to one another.

In accordance with one aspect of the present invention, two carbon-fiber composite materials may be used, alone or in combination, to form one or more medical instruments for temporary or permanent placement in-vivo of the medical instrument or instruments; namely, polyetheretherketon (PEEK) and/or ployetherketonketone (PEKK) may be used. VICTREX® PEEKT, manufactured by the Victrex USA Inc. company of West Chester, Pa., can under certain circumstances offer enhanced rigidity. This material may be radio-translucent to X-rays, however, and thus may need to be doped or coated with radiopaque materials such as gold or platinum to be imaged by X-rays. In accordance with one preferred embodiment, a carbon-fiber composite material having a desired MRI radio-opacity, is produced by Synthes (USA) of Paoli, Pa., the product being identified as a #11.0 350 mm carbon fiber rod (part #394.86). This material and others as set forth above can be used, alone or in combination, for the apparatus and applications as set forth in this application.

The needles, probes and marker assemblies for stereotactic, chemotherapeutic or other drug/substance delivery techniques that are shown in PCT Application No. PCT/US00/19219 and PCT Application Numbers PCT/US01/12204 can be constructed with the above-described carbon-fiber composite and related materials in accordance with the present invention. Examples of the methods of such stereotactic and other drug/substance delivery or monitoring techniques are also shown in PCT Application Nos. PCT/US00/19219 and PCT/US01/12204, the entire contents of both applications of which are expressly incorporated herein by reference.

Figure 2:
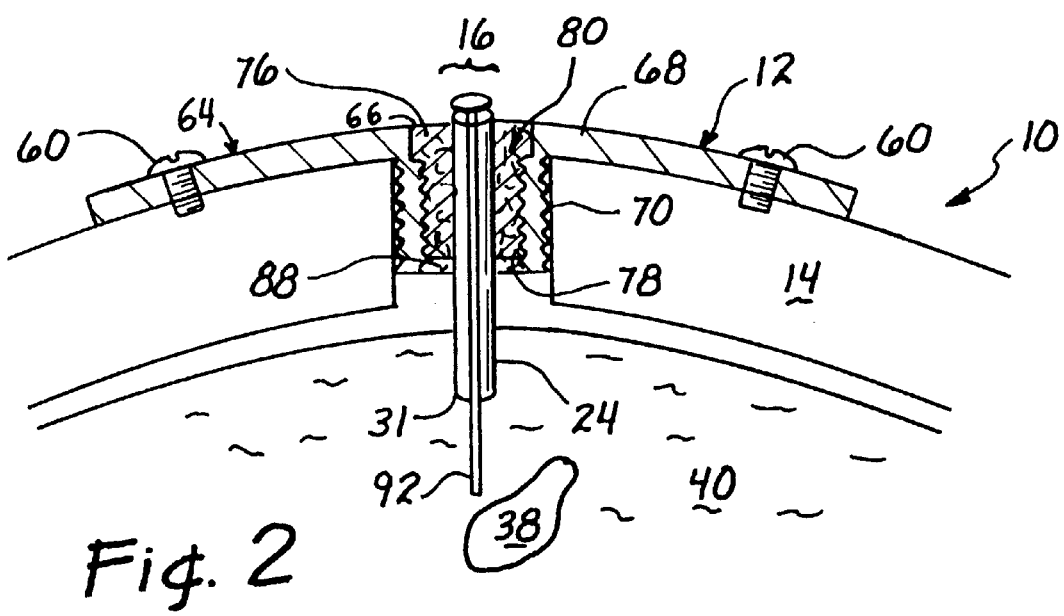
FIG. 2 illustrates a partial cross-sectional view of a carbon-fiber needle apparatus of the present invention being used to locate and treat a target region in the brain.

FIGS. 1 and 2 illustrate an exemplary embodiment of a method and apparatus for utilizing a carbon fiber imaging pointing device, wherein the apparatus 10 comprises: an attachment member 12; a marker assembly comprising a detachable member 24 and a needle 92 (FIG. 2); and a locator device 30. The attachment member 12 is preferably constructed of an Aluminum or non-ferrous material and is adapted to be secured to a cranium 14 of the patient, and the detachable member 24 preferably comprises a cannula. The detachable member 24 is adapted to be connected to the locator device 30. The locator device 30 preferably comprises, for example, a conventional stereotaxic head-frame assembly suitable for positioning a conventional probe within the brain based on predetermined location data, and further comprises an installation probe 34 for use in place of the conventional probe.

In accordance with the present invention, the needle 92 comprise a radiopaque or semi-radiopaque material, that is selected or tailored in accordance with the selected imaging technique to provide higher definition imaging than titanium. As presently preferred, the needle 92 comprises a carbon fiber composite material. The detachable member 24, which preferably comprises porcelain or ceramic, is secured to the attachment member 12; and the needle 92 is preferably inserted through the cannula 24 after the detachable member 24 is secured to the attachment member 12. In an alternative embodiment, the detachable member 24 comprises a material which does not scatter and which provides high resolution under an imaging beam compared to a resolution provided by titanium. For instance, the detachable member 24 can comprise a carbon fiber composite material as described herein.

As will be described in greater detail hereinafter, the detachable member 24 is adapted to be secured to the attachment member 12 and immobilized within the brain. The detachable member 24 is adapted to be disconnected from the locator device 30 after being secured to the attachment member 12 and immobilized within the brain, wherein the detachable member 24 remains immobilized and stationary during and subsequent to the process of being disconnected from the locator device 30.

Increased accuracy is provided in the subsequent placement of the needle 92 wherein additional scans, screenings or other diagnostic procedures can be performed on the patient, with the marker assembly 24, 92 immobilized in place, prior to the patient undergoing subsequent treatment procedures. More specifically, high accuracy imaging techniques can be used to identify, for example, the location of the needle 92 relative to the target region 38 of the brain. The composition of the needle 92 of a bio-compatible carbon-fiber composite material, which during imaging can result in a clear or clearer image relative to the image that would be produced by a titanium needle, can help to facilitate this high-accuracy imaging procedure. The apparatus 10 allows for correction, or refinement, of the placement of the needle 92 based on data obtained in the later verification procedures. Thus, once the marker assembly 24, 92 is accurately placed, for example within about a 1 mm margin of error, for example, treatment of the target region 38 can proceed.

With reference to FIG. 1, the locator device 30 is illustrated comprising a stereotaxic arc 32 with the installation probe 34 extending therefrom. The installation probe 34 is adapted to extend from the stereotaxic arc 32 to a general vicinity of a target region 38 in the brain 40 (FIG. 2). More specifically, the installation probe 34 is configured to be accommodated at one end thereof by the conventional stereotaxic arc 32 and to accommodate at the other end the cannula 24. It can be seen that the installation probe 34 in accordance with the present invention is somewhat modified to include a proximal portion 44 and a distal portion 46, wherein the proximal portion 44 has a diameter larger than a diameter of the distal portion 46. The stereotaxic arc 32 is mounted to the patient cranium by means of a suitable mounting mechanism 50 in order to fix the locator device 30 with respect to the cranium 14.

The cannula 24 is adapted to fit over the distal portion 46 of the installation probe 34, preferably in frictional engagement therewith. The cannula 24 comprises an inner diameter which is about equal to the outer diameter of the distal portion 46 of the installation probe 34. The distal tip 31 of the cannula 24, however, preferably comprises an inner diameter, which is slightly smaller than an inner diameter of the rest of the cannula 24, to thereby enable the cannula to frictionally engage and hold the installation probe 34. The cannula 24 can thus removably engage the distal portion 46 sufficiently securely to prevent the cannula 24 from detaching from the installation probe 34 under, for example, the pull of gravity. The cannula 24 can be readily detached from the installation probe 34 by a surgeon after the installation probe has been positioned in the brain 40 and secured to the attachment member 12. In a preferred embodiment, an outer diameter of the cannula 24 is about equal to an outer diameter of the proximal portion 44 of the installation probe 34.

With reference to FIG. 2, the attachment member 12 is illustrated secured by screws 60 or other fastening members directly to the cranium 14, after an incision has been made in the scalp 63 of the patient. More specifically, the attachment member 12 is secured to an area of the cranium at a desired location determined to directly overlay the target region 38 in the brain. A location of the target region 38 is predetermined by conventional imaging techniques, which are not described in detail herein. The attachment member 12 comprises a disc 64 having an aperture 66 sized to receive the detachable cannula 24. More specifically, the disc 64 comprises a flanged proximal portion 68, hereinafter referred to as a flange or flanged portion. In the illustrated embodiment, the flanged portion 68 has a diameter of about 28 mm. The flanged portion 68 has a radius of curvature that approximates the radius of a human cranium such that the flange 68 lies substantially flat against the cranium. This feature provides a low profile and ensures that the disc 64 can be firmly fixed to the cranium and will remain secure and not become dislocated during the surgical procedure.

It is shown that the attachment member 12 is sized and configured to cover a portion of the cranium surface surrounding and extending into the burr hole. The disc 64 preferably includes a substantially cylindrical distal protrusion 70 extending substantially perpendicularly from the flanged portion 68. The distal protrusion 70 is sized to fit within a burr hole that has been created in the cranial plate, for example by conventional surgical techniques, in order to expose the outer dura of the brain 40. As presently preferred, the outer wall of the distal protrusion 70 should closely fit within the burr hole. In the illustrated embodiment, the burr hole has a diameter of about 14 mm and the maximum diameter of the distal protrusion is about 13 mm. The surgeon may choose from a selection of attachment members 12 in order to match the burr hole diameter, which may vary from, for example, 6 mm to about 16 mm.

The cannula 24 is adapted to be secured to the attachment member 12 and immobilized in a specific angular orientation within the brain 40. This specific orientation is, for example, an orientation in which the locator device 30 was used to position the cannula 24, when the cannula 24 was connected to the distal portion 46 of the installation probe 34 as described above. It is to be appreciated that although the cannula 24 is shown at a generally perpendicular orientation with respect to the cranium surface, the cannula 24 can be disposed in other desirable angular orientations as well.

After being positioned in the brain 40, the cannula 24 is firmly and rigidly secured to the attachment member disc 64 by means of an adhesive 80. By adhesion of the cannula 24 to the attachment member 12, the cannula is fixed and immobilized in a desired orientation within the brain 40 so that an axis of the cannula is calculated to intersect with the target region. As will be described hereinafter, the cannula 24 can than be detached from the locator device 30 by extracting the installation probe 34 from the cannula 24. The needle 92 can then inserted into the immobilized cannula 24 and used as a marker that can be imaged within the brain. Advantageously, the attachment member/cannula combination, i.e. the marker assembly 24, 92 defines a low profile on the cranium surface. This facilitates a surgeon in performing additional scans, for example, verification scans, of the brain 40 without cumbersome and ferrous equipment being connected to the patient. The low profile also enables the surgeon to close the incision 62, maintaining a sterile environment, after removing the installation probe 34 and before performing a verification scan.

In the preferred embodiment shown, the distal protrusion 70 of the attachment member disc 68 defines a reservoir 76, including a grooved wall 78 for receiving the adhesive 80. In this preferred embodiment, the adhesive 80 comprises a catalyzing adhesive, for example a methyl methacrylate that will solidify in a short time period, for example a time period of less than 15 minutes.

Prior to introducing the adhesive 80, it is preferred that a medium is placed into the reservoir 76 between the grooved wall 78 and the cannula 24. In the presently preferred embodiment, the media comprises a commercially available resorbable gel foam 88 that is gently packed or positioned about the cannula 24 in order to prevent the fluid adhesive 80 from entering the cranial cavity. Suitable gel foam is typically provided in absorbable sheets of between about 3 mm and 6 mm in thickness. For use in the present invention, such a gel foam sheet is cut into small pieces and then hydrated, for example with a sterile saline solution which softens the pieces for insertion into the reservoir 76 of the distal protrusion 70. Although it is preferred that the distal protrusion 70 extend deep enough into the burr hole to provide for a great depth of adhesive for strong fixation of the cannula, it is also preferred that the distal protrusion not extend fully through the burr hole to protect the brain. The distal protrusion 70 is thus constructed in the illustrated embodiment to extend greater than half of the distance through burr hole but less than the full thickness of the cranium. In the illustrated embodiment, the burr hole is about 10 mm thick and the distal protrusion extends about 6 mm therethrough, and the layer of gel foam 78 extends about 1 mm to about 2 mm up from the bottom of the distal protrusion.

As shown, the adhesive-filled reservoir 76 at least partially circumscribes a proximal end 86 of the cannula 24 when the cannula 24 is secured to the attachment member 12 as illustrated in FIG. 2 and functions to secure the cannula 24 in a precise location within the brain 40. In other words, the reservoir 76 is structured, when at least partially filled with cured adhesive and when the installation probe 34 is removed from within the cannula 24, to immobilize the cannula 24 at the same orientation as the orientation of the distal portion of the installation probe at a time before the cannula 24 is disconnected from the locator device 30.

The needle 92 is inserted through the immobilized cannula 24 such that a distal end of the needle 92 extends at least as far as the distal tip 31 of the cannula 24. In the illustrated embodiment, the needle 92 extends past the cannula distal tip 31 and marks the target region 38. In accordance with the present invention the needle 92 preferably comprises a rigid, inflexible, high precision element which does not scatter and which provides high resolution under an imaging beam compared to a resolution provided by titanium. As presently embodied, the needle 92 comprises a carbon fiber composite material. The needle 92 preferably includes a lumen (not shown) along a longitudinal axis thereof, through which an active agent, such as a medication can be directly delivered into brain tissue within the target area 38.

As mentioned, the distal protrusion 70 has a depth that is less than a depth of the cranium to which the attachment member 12 is secured. The depth of the attachment member is preferably less than about 10 mm. In addition, the flanged portion 68 will have a diameter that is partially dependent upon the diameter of the burr hole. In addition still, the radius of curvature of the flanged portion 68 will depend upon the radial curvature of the patient's cranium, which is known to vary depending upon the portion of the cranium to which the attachment member will be mounted. Thus, as previously mentioned, it will be appreciated that various sizes and curvatures of attachment members 12 may be made available to accommodate different situations.

In the illustrated embodiment the marker assembly is length adjustable. For example, the marker assembly may comprise a plurality of needles, e.g., carbon fiber needles similar to needle 92, having different lengths. Preferably, each needle 92 comprises a proximal portion with a diameter larger then a diameter of the lumen of the proximal end of the cannula 24. Washers or other spacing means may be inserted between the proximal portion of the needle and the cannula for providing high-precision spacing. Thus, a surgeon can choose a desired length of needle for treating the patient.

In accordance with a method of the present invention, a sterotaxic reference frame, such as the stereotaxic reference frame 50, is attached to the head of a patient via mounting plates 50, and as aperture or burr hole is generated in the cranium of the patient. The dura is also breached at the burr hole, to allow for settling of the brain. At this point, the attachment member 12 may be secured to the cranium 14, centered over the burr hole. Alternatively, the attachment number 12 may be secured at a later point in time.

After the brain has settled, the burr hole wound is closed, by suturing and/or bandaging thereof. The patient, with the stereotaxic reference frame attachment, is then transported to an imaging room in the hospital, for example. As presently preferred, a three-dimensional imaging marker assembly is then secured to the stereotaxic reference frame (e.g., mounting plates 50), and the patient's brain is imaged. The three-dimensional imaging assembly can then be removed, and the patient is brought back into the operating room. At this point, the burr hole wound is reopened, and if not already attached, the attachment member 12 is secured to the cranium 14. The stereotaxic arc 32 is then attached to the stereotaxic reference frame 50, and the imaging data is used to orientate and position the installation probe 34 for incision to the target region, based upon the imaging data obtained in the imaging scan of the patients brain.

At this or an earlier point, the cannula 24 is inserted over the distil portion 46 of the installation probe 34, and the resulting assembly is inserted into the patient's brain and into proximity of the desired target region of the patient's brain. As presently embodied, the installation probe 34 is inserted to a point just shy of the target region within the brain, so that the distil portion 46 and the cannula 24 do not actually extend fully to the target region. For example, the surgeon may determine to have the distil portion 46 of the installation probe 34, and the cannula 24, advanced to a point exactly 10 mm shy of the target region. Subsequently, when the needle 22 is inserted through the cannula 24, the needle 22 will be constructed to extend exactly 10 mm distally of the distil tip 31 of the cannula 24, to thereby extend to the target region.

Once the installation probe 34, with the attached cannula 24, has been inserted to the desired location through the aperture of the attachment member 12, the method of the present invention performs steps to secure the cannula 24 to the attachment member 12 so that the cannula 24 is immobilized within the patient's brain for the subsequent removal of the installation probe 34. In the illustrated embodiment, pieces of hydrated gel foam 88 are carefully inserted through the aperture of the attachment member 12, distally into the protrusion portion 70. Care is of course taken not to bump or press against the cannula 24. The pieces of gel foam 88 preferably form a barrier at the distil end of the protrusion portion 70, so that an adhesive 80, preferably a catalyst and polymer adhesive, can be placed within the protrusion portion 70 with, for example, a syringe. The adhesive 80 preferably sets in about five to fifteen minutes, to thereby fix the orientation of the cannula 24 during and after the subsequent removable of the an installation probe 34.

In accordance with the illustrated method, the installation probe 34 is subsequently withdrawn and the stereotaxic arc 32 removed. At this point, a needle 22 is selected to extend the proper distance beyond the cannula 24 to the target region. The proximal end of the needle 22 preferably comprises a head for abutting against the proximal end of the cannula 24 and, further, washers or other spacing means may be inserted between the proximal end of the needle and the proximal end of the cannula 24, for spacing versatility. Alternatively, a proximal portion of the needle 22 may be threaded, and a washer may be moved up and down the proximal threaded portion to adjust the length of the needle 22 that protrudes distally through the cannula 24.

Once the needle 22 has been carefully positioned within the cannula 24 to extend to the target region, the attachment member 12 can be covered with sutures and/or dressing, and the patient can be transported again to the imaging room for a verification imaging scan to ensure that the distil end of the needle 22 is indeed at the target region. If the verification scan provides data indicating that the needle 22 is on the mark, then the placement procedure is completed, and subsequent treatment procedures of the target region can be conducted. If, on the other hand, the verification scan shows the needle 22 to be off-target, then this data may be used to fine tune the placement of the needle 22. For example, another needle 22 maybe inserted to the proper depth and/or curved needles or memory-material needles maybe used alone or in combination with the needle 22, to reach the proper target region. Moreover, it may be prudent to remove the attachment member 12 and the associated cannula 24 and needle 24, so that the entire method may be repeated and concluded with a subsequent verification imaging scan. If the subsequent imaging yields the proper data, then the procedure may be concluded. If additional placement steps are needed, such as any of the above-discussed steps, then those steps can be conducted until proper placement is obtained. Other less preferred embodiments of the present invention are now described.

Each of the above features disclosed herein is included within the scope of the present invention, which as broadly defined herein comprises a high-definition marker device. In addition all combinations of the presently disclosed features which are not mutually inconsistent or incompatible are also included within the scope of the present invention.

We claim:

1. A marker assembly, comprising:
   a shaft sized and shaped to be inserted into an organ, the shaft comprising a proximal end, a distal end, and a longitudinal axis extending between the proximal end and the distal end, the distal end of the shaft being sized and shaped to be positioned near a target region within the organ; and
   a lumen extending through the shaft in a direction parallel to the longitudinal axis of the shaft, wherein the lumen is constructed to accommodate a longitudinal device therethrough so that the longitudinal device enters through the proximal end of the shaft, extends through the shaft, and exits through the distal end of the shaft;
   wherein the longitudinal device comprises radiopaque or semi-radiopaque materials that provide higher definition imaging when implanted within the organ than titanium.

2. The marker assembly as set forth in claim 1, wherein the marker assembly is structured to be inserted into a brain.

3. The marker assembly as set forth in claim 2, wherein the marker assembly comprises a carbon fiber composition formed of at least one continuous carbon fiber.

4. The marker assembly as set forth in claim 2, wherein the marker assembly comprises a carbon fiber composition.

5. The marker assembly as set forth in claim 4, wherein the marker assembly comprises carbon fibers and a binding resin combined to form a matrix.

6. The marker assembly as set forth in claim 5, wherein the carbon fibers comprise about 40 percent to about 60 percent of the matrix, and the balance of the matrix comprises a resin material.

7. The marker assembly as set forth in claim 6, wherein the longitudinal device is a needle.

8. The marker assembly as set forth in claim 1, wherein the marker assembly comprises a carbon fiber composition comprising at least one continuous carbon fiber.

9. The marker assembly as set forth in claim 1, wherein the marker assembly comprises a carbon fiber composition.

10. The marker assembly as set forth in claim 9, wherein the marker assembly comprises carbon fibers and a binding resin combined to form a matrix.

11. The marker assembly as set forth in claim 10, wherein the carbon fibers comprise about 40 percent to about 60 percent of the matrix, and the balance of the matrix comprises a resin material.

12. The marker assembly as set forth in claim 11, wherein the longitudinal device is a needle.

13. A marker assembly, comprising:
    a needle dimensioned to be advanced through a lumen of a shaft to a location near a target region of an organ, the needle comprising radiopaque or semi-radiopaque materials that provide higher definition imaging when implanted within the organ than titanium.

14. The marker assembly as set forth in claim 13, wherein the needle comprises a carbon fiber composition.

15. The marker assembly as set forth in claim 14, wherein the needle comprises a carbon fiber composition formed of at least one continuous carbon fiber.

16. The marker assembly as set forth in claim 14, wherein the needle comprises carbon fibers and a binding resin combined to form a matrix.

* * * * *